United States Patent [19]
Lautenschlager et al.

[11] Patent Number: 5,902,839
[45] Date of Patent: May 11, 1999

[54] BONE CEMENT AND METHOD OF PREPARATION

[75] Inventors: Eugene P. Lautenschlager, Skokie; Jeremy L. Gilbert, Downers Grove; Peter Monaghan, Elmhurst; Steven J. Duray, Rolling Meadows; Richard L. Wixson, Chicago, all of Ill.

[73] Assignee: Northwestern University, Evanston, Ill.

[21] Appl. No.: 08/758,680

[22] Filed: Dec. 2, 1996

[51] Int. Cl.$^6$ .............................. C08L 33/00; A61L 25/00
[52] U.S. Cl. ...................... 523/115; 523/116; 523/117; 524/533; 524/358; 522/47; 522/902; 606/92
[58] Field of Search ................................. 523/115, 116, 523/117; 524/533, 358; 522/902, 47; 606/92

[56] References Cited

U.S. PATENT DOCUMENTS

| | | | |
|---|---|---|---|
| 4,308,190 | 12/1981 | Walkowiak et al. | 260/29.7 |
| 4,404,327 | 9/1983 | Crugnola et al. | 523/116 |
| 4,547,531 | 10/1985 | Waknine | 523/116 |
| 4,554,686 | 11/1985 | Baker | 623/16 |
| 4,629,746 | 12/1986 | Michl et al. | 523/117 |
| 5,219,897 | 6/1993 | Murray | 523/116 |
| 5,276,070 | 1/1994 | Arroyo | 523/117 |
| 5,334,626 | 8/1994 | Lin | 523/116 |
| 5,554,665 | 9/1996 | Tateosian et al. | 522/908 |

*Primary Examiner*—Andrew E. C. Merriam
*Attorney, Agent, or Firm*—Tilton Fallon Lungmus

[57] ABSTRACT

Orthopedic bone cements of low porosity, prepared by mixing together at least two liquid components under conditions that allow only minimal exposure to air, are disclosed. In a preferred system, each liquid component consists essentially of a solution of a linear (non-crosslinked) polymer or copolymer of methyl methacrylate (PMMA) dissolved in a non-crosslinking methyl methacrylate (MMA) monomer, with one such solution also containing an activator and a polymerization inhibitor and a second solution containing an initiator as well as a polymerization inhibitor. No reinforcing fillers are present, although a small amount (no more than 12% by weight of the total cement composition) of a radiopacifier may be included in the composition. Since polymerization is initiated by mixing together two or more liquid solutions, and such mixing may be performed in a mixing chamber in which no air is required or is introduced during the mixing operation, prior problems of cement porosity and weakness resulting from air entrapment are avoided or greatly reduced while the reliability and reproducibility of the mixing operation are greatly improved.

39 Claims, 2 Drawing Sheets

BONE CEMENT AND METHOD OF PREPARATION

BACKGROUND

Orthopedic bone cement is currently prepared at the time of implantation by mixing together two components, one being a liquid and the other a powder. The liquid is a monomer, typically methyl methacrylate (MMA), which also contains a polymerization activator such as N,N-dimethyl-para-toluidine (a tertiary amine) and an inhibitor such as hydroquinone to prevent the monomer from spontaneously polymerizing. The powder typically consists of small spherical beads (usually about 75 $\mu$m in diameter) of poly(methyl methacrylate) (PMMA) and a small amount of a polymerization initiator such as benzoyl peroxide. Different bone cements sometimes include powders or liquids containing other acrylate polymers or monomers. Such powders also commonly include up to about 12% by weight (of the total cement composition) of a radiopaque material such as barium sulfate. The radiopacifier only serves the purpose of rendering such a bone cement radiopaque, allowing a surgeon to observe by x-ray the location and distribution of cement after surgery, and does not function as a reinforcing filler.

When a surgeon mixes the powder and liquid together, the activator in the monomer solution reacts with the initiator in the powder to produce a free radical form of benzoyl peroxide which in turn reacts with the monomer to initiate the addition polymerization of the monomer.

A problem with the current system is that the powder must have air interspersed therein so that it is sufficiently fluffy to allow mixing with the liquid monomer. Unless the powder is loosely packed, effective mixing of the two components is difficult if not virtually impossible. The result of such fluffiness and the effects of mixing a finely-divided solid and liquid together is that air tends to be entrapped within the reaction mixture and remains after polymerization. The porosity caused by such entrapped air is believed to be highly detrimental to the physical and mechanical properties of bone cements and has been implicated in the failure (by loosening) of cemented prostheses.

A further concern regarding current bone cement technology is the sensitivity of cementation results to a surgeon's technique. Different results are often obtained by different surgeons using the same cement components with different mixing and delivery techniques based solely on the ability or familiarity of the surgeon with those techniques.

Patents on orthopedic bone cements disclose variations of the above-described composition and methodology, but focus essentially on ways of making the powder and liquid components and of mixing them to form cements. In Baker U.S. Pat. No. 4,554,686, powder and liquid are premixed and then frozen to halt the polymerization reaction. Lin U.S. Pat. No. 5,334,626 discloses ways of making fine powders or a range of poly(methyl methacrylate) beads which also contain dispersed barium sulfate. Arroyo U.S. Pat. No. 5,276,070 discloses alternative powders such as butyl methacrylate, and Murray U.S. Pat. No. 5,219,897 prepares powder preforms in which the powder is partially bonded but also has continuous porosity to allow methyl methacrylate monomer liquid to surround and encase the powder.

In the dental materials field, it is known to utilize two-paste systems to produce dental restoratives that contain high percentages of reinforcing fillers in crosslinked polymeric matrices. For example, in Walkowiak et al U.S. Pat. No. 4,308,190, the patentees describe a two-paste system in which one paste contains the initiator (benzoyl peroxide) and the other paste contains an amine activator or accelerator. Both pastes contain polymer beads which, being crosslinked, cannot dissolve in monomer, along with up to 80% by weight of inorganic filler particles for improved physical and mechanical properties, and a binder constituent made primarily from difunctional (crosslinking) methacrylic acid-based monomers.

Waknine U.S. Pat. No. 4,547,531 discloses a two-paste system in which one paste has an initiator (benzoyl peroxide) and the other has the accelerator (tertiary amine); however, such paste also contain difunctional (crosslinking) monomers based on methacrylic acid and 60% to 85% by weight of inorganic filler particles which are typically silanized to enhance bonding with the polymer. The difunctional monomers and the large proportion of filler particles are provided to enhance the physical and mechanical properties of the dental restorative material.

SUMMARY OF THE INVENTION

The bone cement system of this invention is an all-liquid system composed of two or more liquid components that are mixed together just prior to use under conditions allowing only minimal exposure to air. One of the liquid components takes the form of a non-crosslinked linear polymer or copolymer (e.g., PMMA) dissolved in a non-crosslinking monomer (e.g., MMA) along with a suitable polymerization inhibitor to prevent spontaneous polymerization during storage. Another of the liquid components essentially contains either a polymerization activator (e.g., a tertiary amine) or a polymerization initiator (e.g., benzoyl peroxide), with such second solution also optionally containing the same non-crosslinked linear polymer or copolymer dissolved in non-crosslinking monomer as in the first solution. Whichever activator or initiator that is not present in the second solution is included either in the first solution or in a third liquid component. Therefore, when the plurality of liquid components are mixed together just prior to application, the initiator of one component interacts with the activator of another liquid component to produce free radicals that in turn initiate the polymerization of the monomer. Taking the multiple component system as a whole, the weight/volume ratio of polymer to monomer should be in the range of about 0.5:1 to 2:1 g/ml. A small amount of radiopacifier (e.g., barium sulfate in an amount not exceeding about 12% by weight of all components) may be included in one or more of the components to serve as an x-ray imaging agent, such radiopacifier being incapable of involvement in the reaction or of functioning as a reinforcing component.

In a preferred embodiment of the invention, the system comprises at least two viscous liquid solutions each consisting of a linear polymer or copolymer of PMMA completely dissolved in a non-crosslinking monomer (MMA). One solution also has dissolved therein a polymerization inhibitor and one of either a polymerization activator or a polymerization initiator. A second solution containing the same polymer and monomer as the first also contains a polymerization inhibitor and whichever of the polymerization activator and polymerization initiator is not present in the first solution. Each solution therefore takes the form of a viscous liquid where the solvent is the monomer and the solute is the linear (non-crosslinked) polymer which, although dissolved, retains its molecular weight. In one solution is an initiator and in the second an activator, with a suitable inhibitor or antioxidant also being dissolved in each solution. One or both solutions or, if desired, a third solution containing the same monomer and optionally the same dissolved polymer, may include a small amount of a radiopacifier as already indicated.

Each solution is supplied to the user as a liquid premix which may be easily intermixed with the other(s), without the entrapment of air or other gases, at the time of surgery. The use only of liquid components not only eliminates or greatly reduces problems of porosity but also virtually eliminates technique of preparation from the factors affecting bone cement properties. Unlike conventional procedures in which PMMA powder is mixed with MMA monomer at the time of implantation, mixing may occur simultaneously with delivery, or at a selected interval prior to delivery, without variations in proportions and mixing techniques that may affect the properties and qualities of the resulting cement. Most advantageously, the premixed solutions may be contained in separate compartments of a conventional cement gun and be discharged simultaneously from their separate compartments into a mixing chamber where they are intimately blended without introducing air, and then be discharged in mixed and flowable condition either directly to the surgical site or to the single cartridge of an additional gun that is thereafter used to apply the uncured cement to a surgical site.

Other features, advantages and objects will appear from the specification.

DETAILED DESCRIPTION OF PREFERRED EMBODIMENTS

Figure 1:
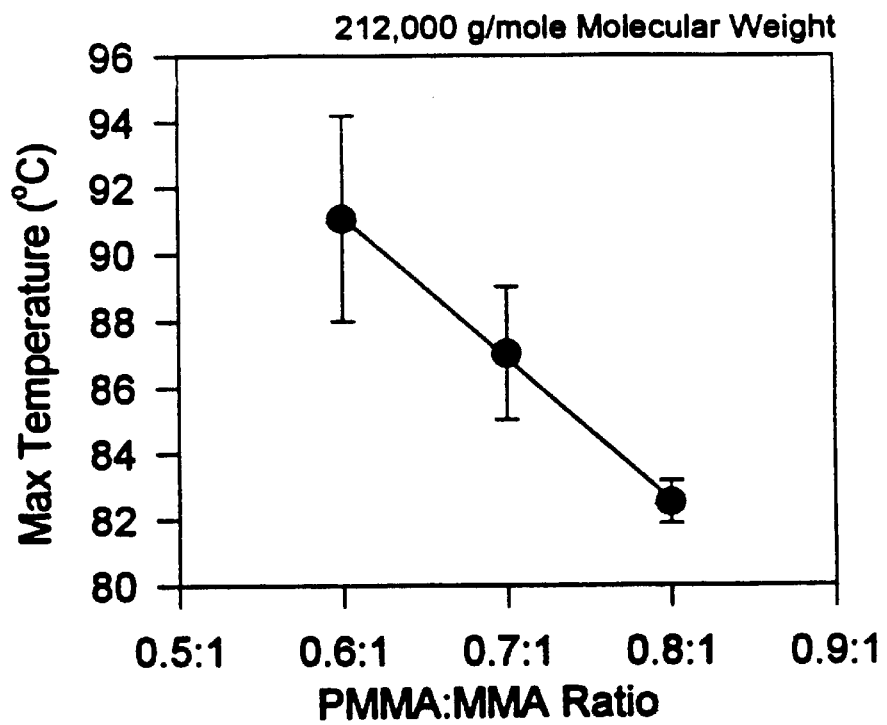
FIG. 1 is a graph depicting maximum setting temperatures for three different polymer/monomer ratios as referenced in Example 3.

The chemical components of a bone cement embodying this invention are essentially the same as those currently used in orthopedic practice. The differences lie not in the chemical composition but in the manner in which the components are combined. In both systems, the procedure involves dissolving a polymer in primarily a monomer liquid to form a solution and then polymerizing the monomer in the presence of an initiator (benzoyl peroxide) and an activator (a tertiary amine) to produce bone cement which is non-crosslinked and unfilled or unreinforced. Unlike prior practice, however, where one part is a powder (primarily PMMA) and the other a liquid (primarily MMA), this invention comprises a system involving two or more liquid components, at least one of which constitutes a solution of a linear polymer or copolymer of methyl methacrylate (PMMA) premixed with and dissolved in monomer (MMA). In such a liquid premix, the linear polymer is dissolved in the non-crosslinking monomer without altering the molecular weight of the polymer, that is, without depolymerizing the polymer.

In a preferred system, there are at least two such liquid premixes in which the linear polymer is dissolved in the non-crosslinking monomer. Liquid premixes containing monomer should also include a small amount of a polymerization inhibitor to prevent spontaneous polymerization. One particularly effective inhibitor is hydroquinone, although other agents having similar inhibitory properties may be used. one form in which MMA is commercially available contains approximately 75 ppm hydroquinone, and it has been found that such amounts of inhibitor are effective here in preventing spontaneous polymerization, although other concentrations within the general range of about 25 to 200 ppm are believed suitable.

Whether the monomer and dissolved polymer are provided in only one liquid premix or in two or more of such premixes, the total weight/volume ratio of polymer to monomer for the system should fall within a range having a lower limit of about 0.5:1 g/ml and an upper limit of about 2:1 g/ml. Particularly effective results have been obtained with a ratio of about 0.7:1 to about 1:1 g/ml, although other ratios within the defined range may be as effective or possibly even more effective.

To initiate free radical polymerization of the monomer, the monomer must be exposed to the reaction product of an activator and an initiator. Since the activator is dissolved in one premix and the initiator in another, and since the premixed liquid components are maintained in separate compartments or cartridges and are not brought together until the cement is required for implantation, each premix may be stored and will remain in stable unpolymerized condition for periods of several months or more.

Benzoyl peroxide is a suitable polymerization initiator for use in this system, although other initiators capable of generating free radicals when reacted with a tertiary amine might be used. The tertiary amine activator may be N,N-dimethyl-para-toluidine. The precise amounts of initiator and activator depend partly on the desired rate of polymerization and the amount needed to produce complete polymerization upon mixing of the premixes while, at the same time, avoiding excessive amounts that might induce spontaneous polymerization prior to mixing. It has been found that incorporating about 0.4% to 10% by volume of benzoyl peroxide and between 0.5% and 3% by volume of N,N-dimethyl-para-toluidine, is sufficient to produce complete polymerization in about 3 to 20 minutes after the two liquid premixes have been blended together, such percentages being based on the total combined volume of monomer present in the system. Lower percentages will result in longer polymerization times whereas higher percentages will increase such rates, with such setting time generally being selected to fall within the range of about 3 to 30 minutes.

The viscosity of each premix may be tailored by varying the ratio of polymer to monomer and the molecular weight of the polymer. For a weight average molecular weight of about 120,000 g/mole (weight average molecular weights falling within the general range of 40,000 to 450,000 g/mole are believed suitable), a ratio of 0.75 to 1 results in a viscous but readily flowable solution. Flowability and workability increase as the proportion of polymer to monomer is reduced, but the heat generated by the exothermic polymerization reaction is increased and becomes an offsetting factor for surgical applications. conversely, increasing the proportion of polymer towards the upper limit of the range reduces the heat exotherm but also renders the liquid components increasingly viscous and may make them unacceptably difficult to mix together or apply the cement during surgery. Similarly, reducing the molecular weight of the polymer will reduce the viscosity of the solution. For a set polymer/monomer ratio, increasing the molecular weight of the polymer has a disadvantage of increasing viscosity but is advantageous in lowering the heat exotherm.

While the polymer of each premix in the preferred system has been described as being PMMA, it is to be understood that variations are acceptable. Thus, the polymerized component of each premix may be a copolymer of methyl methacrylate and styrene as, for example, in the copolymer marketed as Simplex-P by Howmedica, Rutherford, N.J. Similarly, methyl methacrylate monomers which contain some proportion of butyl methacrylate are known and believed suitable for use in this system. In any event, each liquid premix consists essentially of a linear polymer or copolymer of methyl methacrylate dissolved in a non-crosslinking methyl methacrylate monomer, with each premix then also containing either an activator or initiator dissolved in each premix.

Conventional bone cement usually contains a small amount (up to about 12% by weight) of an inert radiopaque agent such as barium sulfate for purposes of x-ray imaging of an implant in which such cement has been used as a fixative. The amount of radiopacifier must be strictly limited because it performs no function as a reinforcing agent and may even have a weakening effect on the fully cured cement. Where needed, such a radiopacifier may be incorporated in this system by simply including up to 12% (of the combined weight of all solutions) in one of the premixes or by including lesser amounts in each of the premixes to bring the total percentage to a level no greater than about 12%. Alternatively, the radiopacifier may be incorporated in a third premix which also contains a non-crosslinking methyl methacrylate monomer and, preferably, the same linear polymer or copolymer of methyl methacrylate dissolved in such monomer.

An important advantage of the multiple all-liquid premix system is that the solutions may be easily mixed or blended together in the surgical arena without introducing air into the mixture, thereby avoiding air entrapment and the undesirable porosity which such entrapment produces. Each premix, being prepared and placed in sealed compartments or cartridges by the manufacturer, may also be produced substantially free of air. At the time of use, the respective cartridges may be placed in a conventional mixing and dispensing gun which, in operation, discharges the premixes into a mixing chamber leading to a discharge nozzle. The mixing chamber may include a mixing impeller to insure that the liquid components are thoroughly mixed prior to discharge. Such an apparatus is commercially available from Semco, Inc., Los Angeles, Calif. and is used for insulating foams, adhering highway markers to concrete, and fuel tank repair. Also, effective results have been achieved using a 50 ml dual cartridge syringe with a 3.5 inch static mixing nozzle as marketed by Ellsworth Adhesive Systems, Germantown, Wis., but other similar guns for mixing miscible solutions in the absence of air and then discharging such solutions in thoroughly mixed condition may be used, similar to those commonly used for dispensing dental impression materials, or the dual syringe systems used for discharging epoxy adhesives.

In any event, the system is also advantageous because it reduces the time required to mix the materials in surgery (as compared with the conventional and involved practice of mixing a powdered polymer and liquid monomer together prior to implantation). Time may also be saved because the all-liquid system of this invention allows the use of cartridges and conventional equipment capable of mixing liquid components, thereby allowing the introduction of the cement at a stage during surgery where it can be immediately used for implant placement. The system also increases the reliability and reproducibility of the mixing operation with less dependence on variations in a surgeon's or nurse's technique. Thus, the quality of the finished cement produced by this system does not depend on the skill of the one who mixes the cement in surgery.

It is to be understood that the reaction mixture need not be applied directly to the surgical site as it is discharged from the mixing chamber of the gun. It may be preferable in some instances to discharge the reaction mixture into an additional cartridge that is then inserted into a conventional gun for application to the implant site, either immediately or after a short predetermined interval.

A further understanding of the invention may be obtained from the following illustrative examples:

EXAMPLE 1

This example illustrates the mixing and setting of a two solution bone cement embodying this invention.

A two solution bone cement system was prepared as follows: Part A contained 11 g poly(methyl methacrylate) (PMMA), 10 ml methyl methacrylate monomer (MMA), (i.e., PMMA/MMA ratio of 1.1:1), 1.0 ml tertiary amine activator (amine), 200 ppm hydroquinone inhibitor (HQ) and 5 g barium sulfate radiopacifier ($BaSO_4$). Part B contained 48 g PMMA, 40 ml MMA (i.e., a PMMA:MMA ratio of 1.2:1), 0.3 g benzoyl peroxide initiator (BPO), 25 ppm HQ and 10 g $BaSO_4$. Both solutions were made with PMMA powder of 83,000 g/mole weight average molecular weight. Both solutions were made by placing the constituents into a partial vaccum mixing device which was set to 20 inches of mercury pressure (i.e., about 66% of atomospheric pressure) and mixed for about 5 to 7 minutes. Then, each solution was allowed to sit for a period of time until any bubbles separated to the top. The solutions were transferred to a mixing cartridge (Semco, Inc., Los Angeles, Calif.) where the smaller volume (part A) was placed in a tube and the larger (part B) in the outer compartment. All air was removed from both containers. Then part A was injected into the volume of part B and the two were thoroughly mixed together with an internal mixing impeller. Because there was no air present, no porosity was introduced on mixing. Then the mixture was dispensed into a mold for setting time and temperature rise measurements as the mixture polymerized into a set mass. This mixture demonstrated a setting time of about 6.5 minutes and a maximum temperature rise of 74° C., was fully set and hard after completion, and was virtually devoid of porosity.

EXAMPLE 2

A series of experiments were performed to assess the variation in setting times and maximum temperature rises associated with a two-solution system where the solutions contained varied amounts of benzoyl peroxide initiator (BPO) and tertiary amine activator (amine). Two solutions were made with the following conditions: both solutions has a PMMA/MMA ratio of 0.6:1, and the PMMA used in these experiments was 120,000 g/mole molecular weight. Into each solution was added varying amounts of amine and hydroquinone (HQ), and the ratio of BPO to amine was varied as in Table 1. Three solutions per test were performed. (In the table, averages of $T$max and test are given along with standard deviation in parentheses.)

TABLE 1

| Solutions A and B | amine, vol % of MMA | BPO/amine molar ratio | HQ, ppm | $T_{max}$, °C | $t_{set}$, min |
|---|---|---|---|---|---|
| 1 | 0.5 | 1.25 | 50 | 91.0 (3.0) | 16.6 (0.73) |
| 2 | 0.75 | 1.50 | 75 | 87.7 (2.2) | 9.7 (0.92) |
| 3 | 1.50 | 1.75 | 100 | 92.5 (4.7) | 4.8 (0.17) |
| 4 | 2.60 | 2.00 | 150 | 96.4 (13.5) | 3.5 (0.72) |

No $BaSO_4$ was added to either solution in these tests. Thus, the major differences present in these solutions is the increase of amine, BPO and HQ.

All solutions were fabricated by placing the appropriate components into parts A and B and then the solutions were rotated on a motorized shaft for 24 to 48 hours at room temperature. After each solution was thoroughly mixed, they were transferred to a two cartridge static mixing gun (Elsworth Adhesive Systems, Germantown, Wis.) in equal proportions and the solutions were stored in a refrigerator until needed. The two solutions were mixed by injecting each simulataneously into a static mixing nozzle where each component fully mixed with its companion solution. Then the mixture was dispensed into a mold for determination of the temperature rise and time to set.

Three tests of each solution combination were performed to determine the maximum temperature rise and time to set. It can be seen from Table 1 that the maximum temperature rise was relatively constant for the four solutions. No statistical difference was noted for the temperature. However, it should be noted that the time to set varied dramatically from a maximum of 16.6 minutes to a minimum of 3.5 minutes depending primarily on the amine amount and ratio of BPO to amine. Both of these factors will significantly affect the setting time and hence setting time can be adjusted with little change in the setting temperature.

Mechanical properties of the set polymers were also determined for the above solutions. Compression tests were performed on samples cut from the setting experiment samples. A length to diameter ratio of 2 to 1 was used on all samples. The compressive yield strength and modulus of the samples was determined from this testing. The results are shown in Table 2. Three tests per sample were performed.

TABLE 2

| Solutions A and B | Yield Stress, MPa | Modulus, GPa |
|---|---|---|
| 1 | 36.7 (2.9) | 1.26 (0.17) |
| 2 | 60.0 (6.0) | 1.82 (0.86) |
| 3 | 90.4 (9.5) | 1.87 (0.57) |
| 4 | 83.4 (9.0) | 1.94 (0.32) |

It can be seen from Table 2 that the strength and modulus values are susceptible to the amount of amine present and the ratio of BPO to amine.

EXAMPLE 3

In this example, the effect of polymer to monomer ratio was investigated. Samples of solutions of polymer dissolved in monomer were prepared with three different PMMA:MMA ratios, specifically, 0.6:1, 0.7:1, 0.8:1. Also, there were some variations in the amount of BPO and HQ present. Table 3 lists the compositions of the three solutions used. In all cases, the PMMA used was of 212,000 g/mole molecular weight. Three tests per condition were performed.

TABLE 3

| PMMA:MMA Ratio | Amine (%) | BPO:amine Ratio | HQ (ppm) |
|---|---|---|---|
| 0.6:1 | 0.5 | 1.25 | 50 |
| 0.7:1 | 0.5 | 1.50 | 100 |
| 0.8:1 | 0.5 | 1.75 | 150 |

It should be noted that PMMA:MMA ratio, quantity of HQ, and BPO:amine ratio all increase in this data. Increasing HQ tends to lower $T_{max}$, while increasing BPO tends to increase $T_{max}$. However, the strongest effect was that of increasing PMMA:MMA ratio in decreasing $T_{max}$. This can be seen in FIG. 1, where the maximum temperature upon setting is plotted versus the PMMA:MMA ratio.

EXAMPLE 4

This example concerns viscosity of PMMA/MMA solutions in relation to the molecular weight of the PMMA and the PMMA:MMA weight/volume ratios. Several PMMA/MMA solutions were prepared by placing PMMA powder and MMA monomer into a container and rotating the container for a period of time, or by placing both into a partial vacuum mixing system and mixing for a period of time. Two weight average molecular weights were investigated: 212,000 g/mole and 40,000 g/mole. The ratio of PMMA to MMA was varied for each molecular weight solution. Table 4 shows the combinations of PMMA:MMA ratio and molecular weight prepared.

TABLE 4

| Molecular Weight, g/mole | PMMA:MMA ratio |
|---|---|
| 212,000 | 0.5, 0.6, 0.7, 0.8 |
| 40,000 | 0.6, 1.0, 1.5 |

Figure 2:
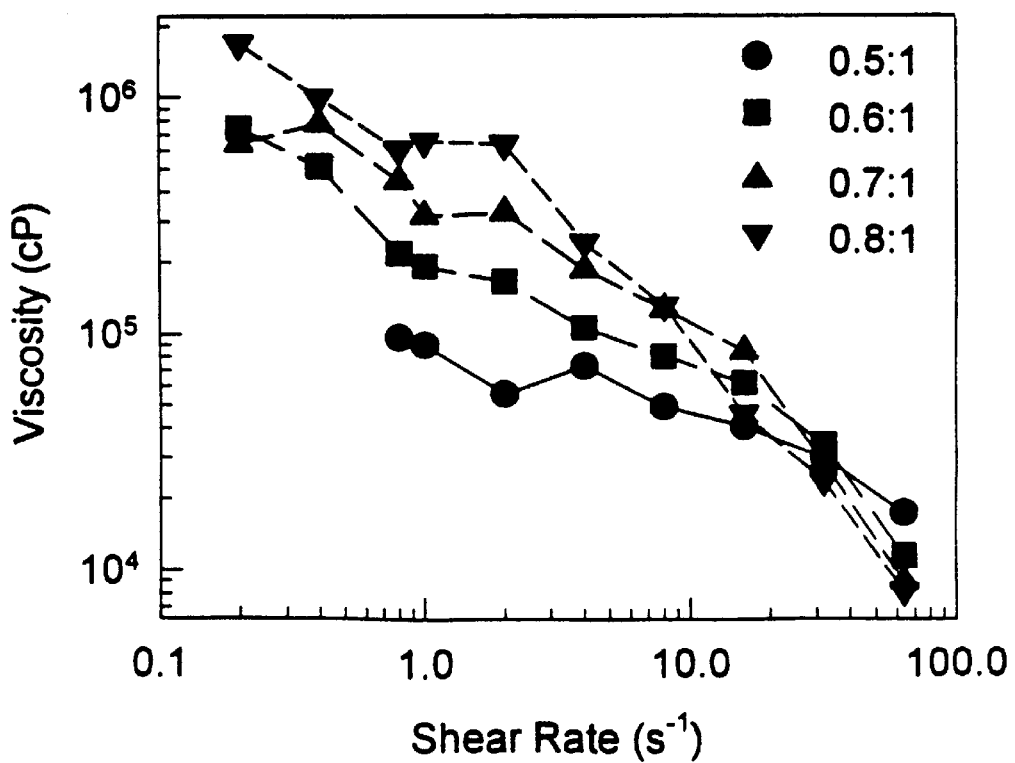
FIG. 2 is a graph illustrating the relationship between viscosity and shear rate for four different polymer/monomer ratios as referenced in Example 4.

In each case, the viscosity of the solutions was measured using a cone and plate viscometer. For the 212,000 MW solutions, the viscosity was measured as a function of shear rate ($s^{-1}$) from 0.2 to 364 $s^{-1}$. The results of this experiment presented in FIG. 2 show that the viscosity of the solutions increases with increasing polymer fraction but that viscosity also decreases with increasing shear rate. This points to the pseudoplastic nature of the solutions and demonstrates that it is possible to make the solutions reach a lower viscosity with the appropriate mixing and ejecting methodology.

Figure 3:
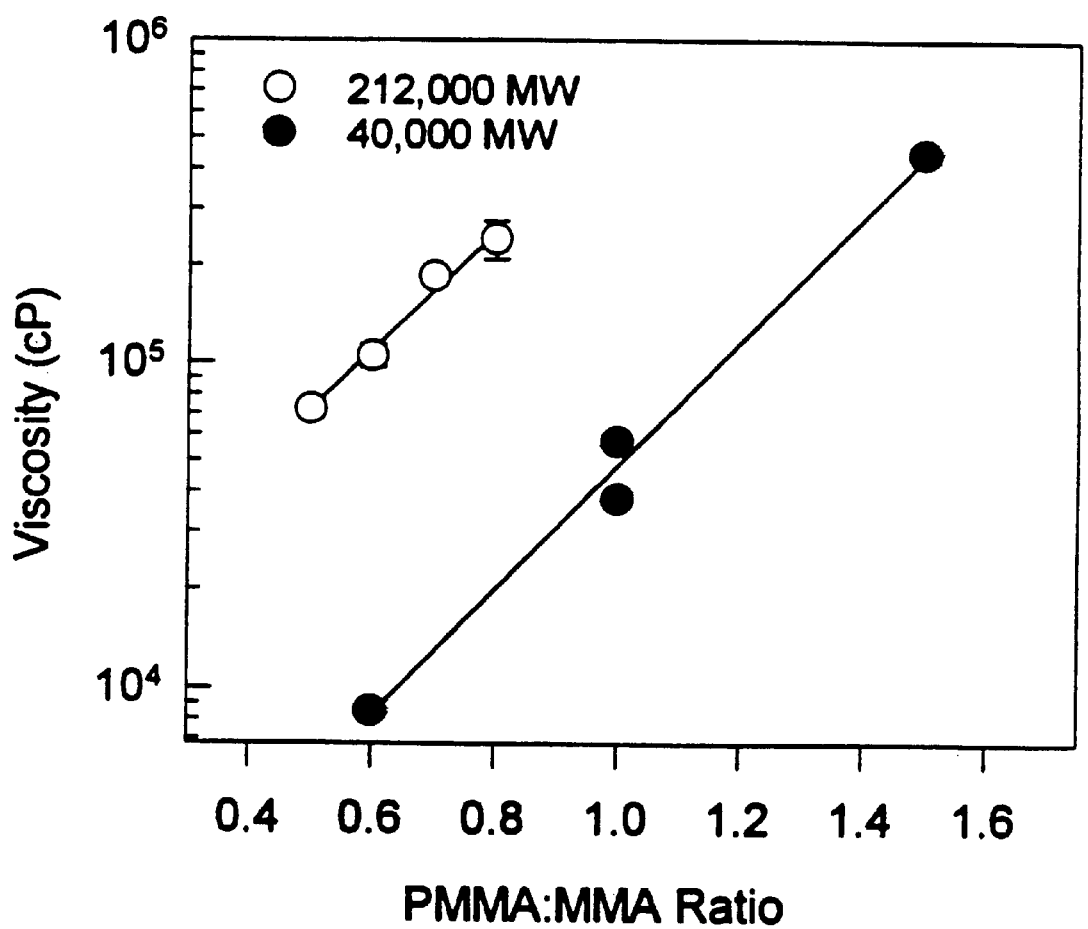
FIG. 3 is a graph showing the relationship between viscosity and polymer/monomer ratios for polymers of two different molecular weights as referenced in Example 4.

A significant flexibility is available to make solutions with systematically controlled viscosity based on the ratio of PMMA to MMA and the molecular weight of the PMMA. This can be seen in FIG. 3, where the viscosity (in centipoise, cP) is plotted against the PMMA:MMA ratio for a constant shear rate of $4s^{-1}$. Two curves are present in this Figure : 1) Solutions made from 212,000 g/mole PMMA and 2) and solutions made from 40,000 g/mole PMMA. From FIG. 3 it can be seen that the viscosity for a fixed PMMA:MMA ratio is significantly lower for the 40,000 MW solutions compared to the 212,000 MW solutions. In other words, greater amounts of PMMA (i.e., higher PMMA:MMA ratio) can be placed into solutions to obtain the same viscosity if the PMMA is lower in molecular weight. This demonstrates the ability to selectively control the viscosity of the solutions based on both the ratio of PMMA:MMA and the molecular weight of the original PMMA powder.

EXAMPLE 5

There are several methods by which solutions of linear polymers or copolymers of PMMA in non-crosslinking MMA monomer can be prepared. These include typical mixing apparatus, rotating drum assemblies, mixing under partial vacuum and warming of the solutions during mixing. Which is used depends in part on the conformation of the starting polymer.

For example, when using a fine powder form (e.g. 75 $\mu$m) for the PMMA, dissolution occurs fairly rapidly, whereas when larger pellets (e.g. 4 mm) are used dissolution of PMMA in MMA may take longer. The mixtures can have all components added at once and then just allowing the solutions to be mixed for a period of time. It is also important to note, however, that the dissolution of the amine and particularly the BPO in their respective solutions of monomer can take place prior to the addition of PMMA. This will assist in the uniform distribution of these activators and initiators. Subsequent dissolution of the PMMA can then take place. Additions of $BaSO_4$ can also take place at t he beginning or at the time when the polymer is added. After mixing and allowing the solutions to sit, it was noted that they were virtually devoid of porosity.

As an example of one typical mixing method, 40 ml MMA, 30 g of a very fine powdered PMMA (about 50 to 100 $\mu$m in diameter), 2.2 ml of amine, 5 g of $BaSO_4$ and 75 ppm of HQ were placed in a partial vaccum mixing system and a partial vacuum was imparted (20 in Hg). T his solution was then mixed at a frequency of about 1 to 2 Hz for 5 to 7 minutes. After this time, the mixture was transferred to a mixing cartridge for combination with its corresponding second solution. After sitting upright for a period of time it was noted any porosity which may have been present had migrated to the top of the solution and was eliminated from the solution.

In another example of processing of solutions, 200 ml of MMA, 120 g of PMMA, 2 wt % BPO and 75 ppm HQ were placed into a polyethylene bottle. The PMMA in this case was from pellets about 4 to 6 mm in length and 2 to 4 mm in diameter. This bottle was then placed on a rotating shaft and allowed to rotate at about 1 Hz for 48 hours at room temperature. After this period, the solutions were uniform and all of the constituents were dissolved. After allowing the solution to stand for another 4 to 6 hours, it was noted that the solution was virtually devoid of porosity.

EXAMPLE 6

This example relates to the mixing and delivery of systems involving two or more solutions.

The manner of mixing and delivering liquid components in the all-liquid bone cement system of this invention depend in part on the composition, number, and volume of such components. For example, if two solutions are made with equal portions of the amine containing solution and the BPO containing solution (with each solution containing PMMA dissolved in MMA), they each can subsequently be placed into cartridges similar to those used for two component epoxy glues. At the end of each cartridge is a hole through which the solutions can be dispensed. If both cartridges are inserted into a dispensing gun and to the end of each cartridge is attached a static mixing nozzle, then the two components can be dispensed into the static mixing nozzle to be mixed and dispensed simultaneously. In the static mixing nozzle, the two components travel through a tube which has fins or protruding vanes which divert each component into the path of the other, substantially mixing the two together. If the nozzle is long enough, by the time the material exits the end of the nozzle, it is thoroughly mixed and ready for delivery to the site.

In another example, the two components, one containing the amine and the other containing the BPO (both containing PMMA dissolved in MMA) can be placed into a mixing system in which one component is in a smaller proportion to the other. The essential feature of this type of mix is that the quanities of amine and BPO are determined by the total quantity of monomer present in both solutions. Thus, if the smaller volume solution contains the amine, the quantity of amine is determined by the total amount of monomer present in both solutions. The mixing system used in this case would be one in which the compartment sizes for each mixture would be different, but that there would be no air present after the solutions were in place. Also, it should be the case that after the two components are introduced to each other, the two can be mixed by an internal impeller inside the chamber without the introduction of air or induction of porosity. Then, after a period of mixing inside the chamber, an exit port is opened to allow the mixed solutions to be dispensed through a tube and delivered to the site. An example of a mixing system of this type was one made by Semco, Inc., Los Angeles, Calif., and is commercially available.

More than two solutions could be combined during mixing to result in essentially the same final set polymer. For example, one solution may be provided in which there is only MMA, PMMA, a small amount of HQ, and $BaSO_4$. This solution may be, by far, the largest volume component to be mixed. Two other solutions could then be introduced and mixed with this first solution. The latter two solutions could contain, for example, MMA, BPO and HQ in one, and amine alone in the other. (BPO, normally a solid available in powder form, would be pre-dissolved in the MMA.) It may be noted that the level of HQ in the component containing BPO dissolved in MMA could be increased significantly to inhibit spontaneous polymerization in that component without raising overall level of HQ in the entire system. That is, the amount of HQ needed in the first solution could be correspondingly reduced because of the lack of initiator or activator in the first solution.

The two latter components would then be introduced to the larger first component and thoroughly mixed with it for a period of a few minutes prior to dispensing and delivery to the site.

Another example, similar to the above, would have the BPO in MMA but also the amine in MMA as well. In that case, there would be three solutions, the first containing PMMA, MMA, $BaSO_4$ and HQ, the second containing MMA, BPO and HQ, and the third containing MMA, amine and HQ.

Other variations of three component systems are believed operative. For example, $BaSO_4$ and MMA only may be present in one liquid component, PMMA, MMA and amine in a second component, and PMMA, MMA and BPO in a third component. Again, if the amount of BPO and amine are set for the entire volume of MMA, such a three-component system should operate effectively.

In the above description concerning mixing and delivery, it is to be understood that the cartridges used for such operations may or may not be the same. Mixing cartridges are those where the two or more components are mixed together, and a delivery cartridge is one where the cement mixture is delivered to the site. In some cases they are the same (e.g., the static mixing system, or the aforementioned Semco mixing system). In some cases they are different (e.g., a static mixing cartridge or nozzle to mix the cement which is then transferred to a second (delivery) cartridge or syringe for subsequent application to the site).

While in the foregoing we have disclosed embodiments of this invention in considerable detail, it will be understood by those skilled in the art that many of these details may be varied without departing from the spirit and scope of the invention.

We claim:

1. An all-liquid bone cement product free of reinforcing fillers and consisting of a plurality of liquid components in separate containers to be mixed and reacted together with only limited exposure to air to produce a polymerized bone cement; one of said liquid components comprising a first solution consisting essentially of a linear polymer or copolymer of poly(methyl methacrylate), and a polymerization inhibitor, completely dissolved in a non-crosslinking monomer; another of said liquid components comprising a second solution of one of either a polymerization activator or a polymerization initiator; said product also comprising one of said plurality of liquid components, other than said second solution, having dissolved therein whichever of said polymerization activator and said polymerization initiator is not present in said second solution; the ratio by weight/volume of said polymer to said monomer in said plurality of liquid components taken together being within the range of about 0.5:1 to about 2:1 g/ml.

2. The product of claim 1 in which said second solution also includes said linear polymer of copoylmer of poly (methyl methacrylate, and a polymerization inhibitor, dissolved in said non-crosslinking monomer.

3. The product of claims 1 or 2 in which said non-crosslinking monomer is methyl methacrylate.

4. The product of claims 1 or 2 wherein said initiator is benzoyl peroxide and said activator is N,N-dimethyl-para-toluidine.

5. The product of claim 4 in which said benzoyl peroxide and said N,N-dimethyl-para-toluidine are present at between 0.4% to 10% and 0.5% to 3%, respectively, of the combined volume of said plurality of liquid components.

6. The product of claims 1 or 2 in which said polymerization inhibitor is hydroquinone and is present in said system within the range of 25 ppm to 200 ppm of the combined volume of all of said liquid components.

7. The product of claims 1 or 2 in which at least one of said liquid components including said non-crosslinking monomer contains finely-divided particles of a radiopacifier in which the amount of said radiopacifier does not exceed 12% of the combined weight of all of said liquid components.

8. The product of claim 7 in which a third liquid solution is provided; said third liquid solution consisting essentially of said non-crosslinking monomer; said radiopacifier being dispersed in said third solution.

9. The product of claims 1 or 2 in which said one of said plurality of liquid components having dissolved therein whichever of said polymerization activator and said polymerization initiator is not present in said second solution comprises said first solution.

10. The product of claims 1 or 2 in which said one of said plurality of liquid components having dissolved therein whichever of said polymerization activator and said polymerization initiator is not present in said second solution comprises a third solution.

11. The product of claim 10 in which said third solution also includes said non-crosslinking monomer and a polymerization inhibitor dissolved therein.

12. The product of claim 11 in which said third solution also includes said linear polymer or copolymer of poly (methyl methacrylate) dissolved in said non-crosslinking monomer.

13. An all-liquid bone cement product free of reinforcing fillers and consisting of a plurality of liquid components in separate containers to be mixed and reacted together with only limited exposure to air to produce a polymerized bone cement; one of said liquid components comprising a first solution consisting essentially of a linear polymer or copolymer of poly(methyl methacrylate), and a polymerization inhibitor, completely dissolved in a non-crosslinking monomer; another of said liquid components comprising a second solution of said non-crosslinking monomer in which is dissolved a polymerization inhibitor and a polymerization initiator; said product also comprising one of said plurality of liquid components other than said second solution including a polymerization activator; the ratio by weight/volume of said polymer to said monomer in said plurality of liquid components taken together being in the range of about 0.5:1 to about 2:1 g/ml.

14. The product of claim 13 in which said second solution also includes said linear polymer or copolymer of poly (methyl methacrylate) dissolved in said non-crosslinking monomer.

15. The product of claims 13 or 14 in which said non-crosslinking monomer is methyl methacrylate.

16. The product of claims 13 or 14 wherein said initiator is benzoyl peroxide and said activator is N,N-dimethyl-para-toluidine.

17. The product of claim 16 in witch said benzoyl peroxide and said N,N-dimethyl-para-toluidine are present at between 0.4% to 10% and 0.5% to 3%, respectively, of the combined volume of said plurality of liquid components.

18. The product of claims 13 or 14 in which said polymerization inhibitor is hydroquinone and is present in said system within the range of 25 ppm to 200 ppm of the combined volume of all of said liquid components.

19. The product of claims 13 or 14 in which at least one of said liquid components including said non-crosslinking monomer contains finely-divided particles of a radiopacifier in which the amount of said radiopacifier does not exceed 12% of the combined weight of all of said liquid components.

20. The product of claim 19 in which a third liquid solution is provided; said third liquid solution consisting essentially of said non-crosslinking monomer; said radiopacifier being dispersed in said third solution.

21. An all-liquid bone cement product free of reinforcing fillers and consisting of at least two liquid components in separate containers to be mixed and reacted together with limited exposure to air to produce a polymerized bone cement; one of said components comprising a first liquid solution consisting essentially of a linear polymer or copolymer of poly(methyl methacrylate) completely dissolved in a non-crosslinking monomer; said first solution also having dissolved therein a polymerization inhibitor and one of either a polymerization activator or a polymerization initiator; another of said components comprising a second liquid solution consisting essentially of said non-crosslinking monomer in which is dissolved a polymerization inhibitor and whichever of said polymerization activator and said polymerization initiator is not present in said first liquid solution; the ratio by weight/volume of said polymer to said monomer in said plurality of liquid components taken together being within the range of about 0.5:1 to about 2:1 ml.

22. The product of claim 21 in which said second solution also includes said linear polymer of copolymer of poly (methyl methacrylate) dissolved in said non-crosslinking monomer.

23. The product of claims 21 or 22 in which said non-crosslinking monomer is methyl methacrylate.

24. The product of claims 21 or 22 wherein said initiator is benzoyl peroxide and said activator is N,N-dimethyl-para-toluidene.

25. The product of claim 24 in which said benzoyl peroxide and said N,N-dimethyl-para-toluidine are present at between 0.4% to 10% and 0.5% to 3%, respectively, of the combined volume of said plurality of liquid components.

26. The product of claims 21 or 22 in which said polymerization inhibitor is hydroquinone and is present in said system within the range of 25 ppm to 200 ppm of the combined volume of all of said liquid components.

27. The product of claims 21 or 22 in which at least one of said liquid components including said non-crosslinking monomer contains finely-divided particles of a radiopacifier in which the amount of said radiopacifier does not exceed 12% of the combined weight of all of said liquid components.

28. The product of claim 27 in which a third liquid solution is provided; said third liquid solution consisting essentially of said non-crosslinking monomer; said radiopacifier being dispersed in said third solution.

29. A method of making bone cement comprising the step of mixing together a plurality of premixed liquid components, each free of reinforcing fillers, under substantially air-free conditions to prevent air entrapment and avoid porosity in the resulting cement; one of said premixed liquid components comprising a first solution consisting essentially of a linear polymer or copolymer of poly (methyl methacrylate), and a polymerization inhibitor, completely dissolved in a non-crosslinking monomer; another of said liquid components comprising a second solution of one of either a polymerization activator or a polymerization initiator; one of said plurality of liquid components, other than said second solution, having dissolved therein whichever of said polymerization activator and said polymerization initiator is not present in said second solution; the ratio by weight/volume of said polymer to said monomer in said plurality of liquid components taken together being within the range of about 0.5:1 to about 2:1 g/ml.

30. The method of claim 29 in which said second solution also includes said linear polymer or copolymer of poly (methyl methacrylate), and a polymerization inhibitor, dissolved in said non-crosslinking monomer.

31. The method of claims 29 or 30 in which said non-crosslinking monomer is methyl methacrylate.

32. The method of claims 29 or 30 wherein said initiator is benzoyl peroxide and said activator is N,N-dimethyl-para-toluidine.

33. The method of claims 29 or 30 in which at least of said liquid components includes finely-divided particles of a radiopacifier dispersed in said non-crosslinking monomer; said amount of said radiopacifier not exceeding 12% of the combined weight of all of said liquid components.

34. The method of claims 29 or 30 in which said one of said plurality of liquid components having dissolved therein whichever of said polymerization activator and said polymerization initiator is not present in said second solution comprises said first solution.

35. The method of claims 29 or 30 in which said one of said plurality of liquid components having dissolved therein whichever of said polymerization activator and said polymerization initiator is not present in said second solution comprises a third solution.

36. The method of claim 29 in which there is the further step of dispensing said reaction mixture in flowable form and substantially free of entrapped air at a receiving site.

37. A method for making bone cement, comprising the steps of preparing a first liquid solution by completely dissolving a linear polymer or copolymer of methyl methacrylate in a non-crosslinking methyl methacrylate monomer, along with a polymerization activator and a polymerization inhibitor, to provide a first liquid premix, free of reinforcing fillers, in which the weight/volume ratio of polymer to monomer is in the range of about 0.5:1 to 2:1 g/ml; preparing a second viscous liquid solution by completely dissolving a linear polymer or copolymer of methyl methacrylate in a non-crosslinking methyl methacrylate monomer, along with a polymerization initiator and a polymerization inhibitor, to provide a second liquid premix, free of reinforcing fillers, in which the weight/volume ratio of polymer to monomer is in the range of about 0.5:1 to 2:1 g/ml; and mixing said first and second liquid premixes together under conditions restricting air exposure thereto to prevent air entrapment in the reaction mixture and avoid porosity in the resulting bone cement.

38. The method of claim 37 in which there is the further step of dispensing said reaction mixture of said first and second liquid premixes at an application site before said mixture has fully polymerized.

39. The method of claim 38 which includes the step of placing said liquid premixes into separate holding chambers communicating with a mixing chamber, and thereafter discharging said liquid premixes from said holding chambers into said mixing chamber without introducing air into said mixing chamber.

* * * * *